US00PP09657P

United States Patent [19]

Zary

[11] Patent Number: Plant 9,657

[45] Date of Patent: Oct. 15, 1996

[54] FLORIBUNDA ROSE PLANT NAMED 'JACJUBEL'

[75] Inventor: Keith W. Zary, Thousand Oaks, Calif.

[73] Assignee: Bear Creek Gardens, Inc., Medford, Oreg.

[21] Appl. No.: 491,143

[22] Filed: Jun. 16, 1995

[51] Int. Cl.[6] ..... A01H 5/00

[52] U.S. Cl. ..... Plt./24

[58] Field of Search ..... Plt./24, 15

[56] References Cited

U.S. PATENT DOCUMENTS

P.P. 6,010 9/1987 Warriner ..... Plt./22

*Primary Examiner*—Howard J. Locker

*Attorney, Agent, or Firm*—Klarquist Sparkman Campbell Leigh & Whinston, LLP

[57] ABSTRACT

A new floribunda rose variety having light yellow flowers of old-rose form borne in clusters and singly; dark green, disease-resistant foliage; and compact growth.

1 Drawing Sheet

The present invention relates to a new and distinct variety of rose plant of the floribunda class which was originated by me by crossing the variety KOResia, U.S. Plant Pat. No. 3,509, with the variety Silver Jubilee, not patented.

The primary objective of this breeding was to produce a new rose variety having the fragrance, yellow flower color, clustering flower habit and compact growth of the female parent combined with the glossy, disease-resistant foliage of the male parent. The objective was substantially achieved, along with other desirable improvements, as evidenced by the following unique combination of characteristics that are outstanding in the new variety and that distinguish it from its parents, as well as from all other varieties of which I am aware:

1. Dark green, glossy, disease-resistant foliage.
2. Light yellow flowers.
3. Clustering flower habit.
4. Compact growth.
5. Fragrant flowers.
6. Old-rose flower form.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—KOResia U.S. Plant Pat. No. 3,509.

*Pollen parent.*—Silver Jubilee (not patented).

Classification:

*Botanical.*—Rosa hybrida.

*Commercial.*—Floribunda.

FLOWER

Observations made from specimens grown in a garden environment at Somis, in Calif.

Blooming habit: Continuous.

Bud:

*Size.*—1¼" long when the petals start to unfurl.

*Form.*—The bud form is short and pointed ovoid.

*Color.*—When sepals first divide, bud color is Green-Yellow Group 154C, but quickly becomes Yellow Group 10C except at the petal base, where it is Yellow Group 10A. When half blown, the upper sides of the petals are Yellow Group 10C; and the lower sides of the petals are Yellow Group 10C.

*Sepals.*—Color: Green Group 138C. Surface texture: Covered in fine hairs. There are three normally to heavily appendaged sepals. There are two unappendaged sepals with hairy edges.

*Receptacle.*—Color: Green Group 137D. Shape: Funnel. Size: Small (3/16"×3/16"). Surface: Smooth.

*Peduncle.*—Length: Medium (2½"). Surface: Smooth. Color: Medium green. Strength: Stiff and erect.

Bloom:

*Size.*—Medium. Average open size is 3½–4 inches.

*Borne.*—Singly and several together, in rounded clusters of 3–7 flowers.

*Stems.*—Medium and strong. Average length is about 14–16 inches.

*Form.*—When first open: Cupped. Permanence: Outer petals curl back.

*Petalage.*—Number of petals under normal conditions: 40–50.

*Color.*—The upper side of the petals is Yellow Group 10C. The reverse side of the petals is Yellow Group 10C. The base of each petal has a Yellow Group 10A half-moon (¼"×¼") at its point of attachment. The major color on the upper side is Yellow Group 10C.

*Varigations.*—None.

*Discoloration.*—The general tonality at the end of the first day: None. At the end of the third day: Little change. At day 5 there is some fading, especially in bright light, to Yellow Group10D.

*Fragrance.*—Moderate.

Petals:

*Texture.*—Thin.

*Shape.*—Round on the outer petals, but becoming spatulate on the inner petals.

*Form.*—Tips slightly recurved on the outer petals.

*Arrangement.*—Imbricated on the outer petals, irregular and sometimes quartered, with few petaloids in the center.

*Persistence.*—Hang on and dry.

*Lastingness.*—On the plant: Fair (5–6 days). As a cut flower: Fair (7 days).

Reproductive parts:

*Anthers.*—Size: Medium. Quantity: Many. Color: Yellow. Arrangement: Regular around styles.

*Filaments.*—Color: Yellow.

*Pollen.*—Color: Gold Yellow.

*Styles.*—Color: Greenish-white.

*Stigmas.*—Color: Yellow.

Form: Bush.

Growth: Medium, vigorous, upright and branching; at maturity (one year without pruning) plant is about 3½' tall and 3' wide.

Foliage:

*Number of leaflets on normal mid-stem leaves.*—5 or 7.

*Size.*—Medium (5" long ×3" wide).

*Quantity.*—Abundant.

*Color.*—New foliage: Close to Green Group 143A but edged in red on the newest growth. Old foliage: Upper surface: Green Group 139A; Lower surface: Green Group 139B.

Leaflets:

*Shape.*—Pointed oval.

*Texture.*—Upper side: Leathery and glossy.

*Edge.*—Serrated.

*Serration.*—Single and small.

*Petiole rachis.*—Color: Green, except on newest foliage, then reddish.

*Petiole underside.*—Smooth with occasional prickles.

*Stipules.*—Medium (½"), smooth and bearded.

Disease resistance.—Resistant to mildew and rust under normal growing conditions at Somis, Calif.

Wood:

*New wood.*—Color: Light Green. Bark: Smooth.

*Old wood.*—Color: Green. Bark: Smooth.

Prickles:

*Quantity.*—On main canes from base: Many. On laterals from main canes: Many.

*Form.*—Short (3/16") and hooked slightly downward.

*Color when young.*—Green

Small prickles:

*Quantity.*—On main stalks: Few. On laterals: Few.

*Color.*—Brown.

I claim:

1. A new and distinct variety of rose plant of the floribunda class, substantially as herein shown and described, characterized particularly as to novelty by the unique combination of its fragrant flowers of light yellow borne in clusters and singly; its dark green, disease-resistant foliage; its compact growth; and its old-rose flower form.

* * * * *

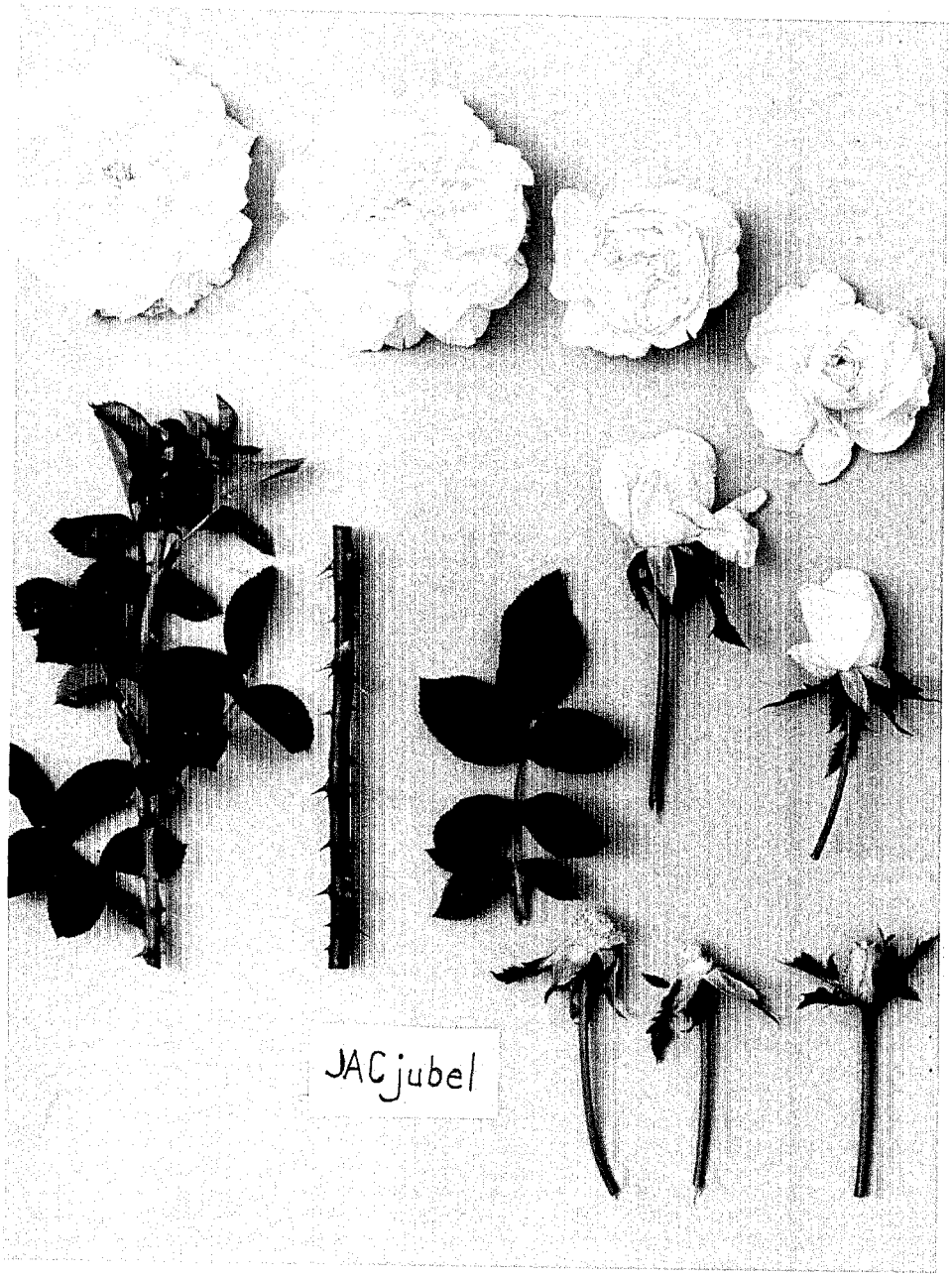
JACjubel

UNITED STATES PATENT AND TRADEMARK OFFICE

CERTIFICATE OF CORRECTION

PATENT NO. : PP 9657

DATED : October 15, 1996

INVENTOR(S) : Keith W. Zary

It is certified that error appears in the above-identified patent and that said Letters Patent is hereby corrected as shown below:

Column 1, line 3, "KOResia" should read –KORresia--;

Column 1, line 37, "KOResia" should read --KORresia--;

Column 2, line 32, "Varigation" should read --Variegations--;

Column 2, line 36, "GroupIOD" should read –Group IOD--.

Signed and Sealed this

Twenty-ninth Day of September, 1998

*Attest:*

*Attesting Officer*

BRUCE LEHMAN

*Commissioner of Patents and Trademarks*